United States Patent [19]

Curcio

[11] Patent Number: 4,868,929
[45] Date of Patent: Sep. 26, 1989

[54] ELECTRICALLY HEATED SKI GOGGLES

[76] Inventor: Philip L. Curcio, 7 Jarvis Ave., Syosset, N.Y. 11791

[21] Appl. No.: 191,361

[22] Filed: May 9, 1988

[51] Int. Cl.$^4$ ............................................. A61F 9/02
[52] U.S. Cl. ............................................. 2/435; 2/436; 219/211
[58] Field of Search ................. 2/435, 436, 437, 426, 2/171.3, 8, 6; 219/211

[56] References Cited

U.S. PATENT DOCUMENTS

| | | | |
|---|---|---|---|
| 3,168,748 | 2/1965 | Limberg | 2/171.3 |
| 3,657,740 | 4/1972 | Cialone | 2/171.3 X |
| 4,150,443 | 4/1979 | McNeilly | 2/171.3 X |
| 4,638,728 | 1/1987 | Elenewski | 2/435 X |
| 4,682,007 | 7/1987 | Hollander | 2/435 X |

FOREIGN PATENT DOCUMENTS

| | | | |
|---|---|---|---|
| 0636251 | 5/1983 | Switzerland | 2/435 |
| 0264280 | 1/1927 | United Kingdom | 2/435 |
| 0699465 | 11/1953 | United Kingdom | 2/436 |

Primary Examiner—Peter Nerbun
Attorney, Agent, or Firm—Michael I. Kroll

[57] ABSTRACT

An improved ski goggles is provided and includes a protective lens that has a fine grid of heat generating wire with sufficient resistance to produce enough heat to remove frost and fog from the lens. An external of self contained battery pack and switching device supplies electricity to the resistance wire grid.

10 Claims, 1 Drawing Sheet

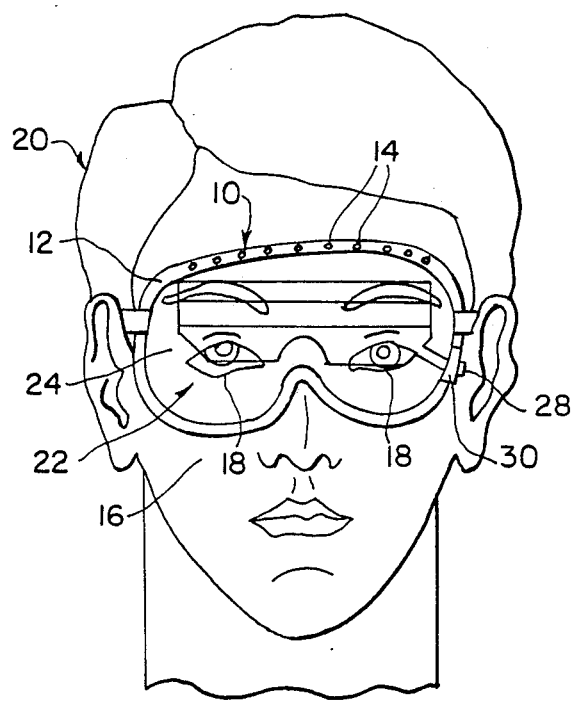
Figure 1
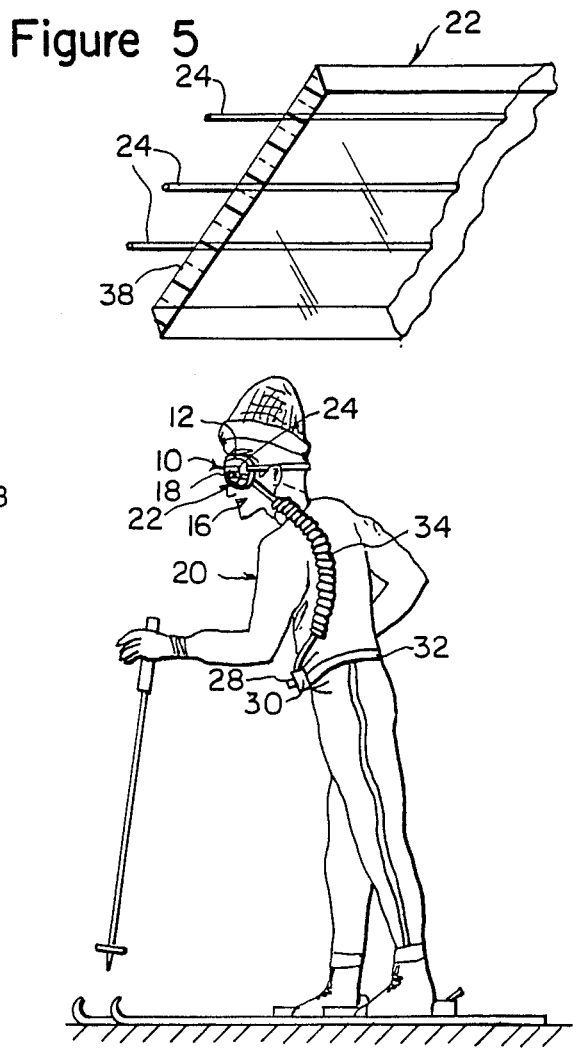
Figure 5
Figure 2
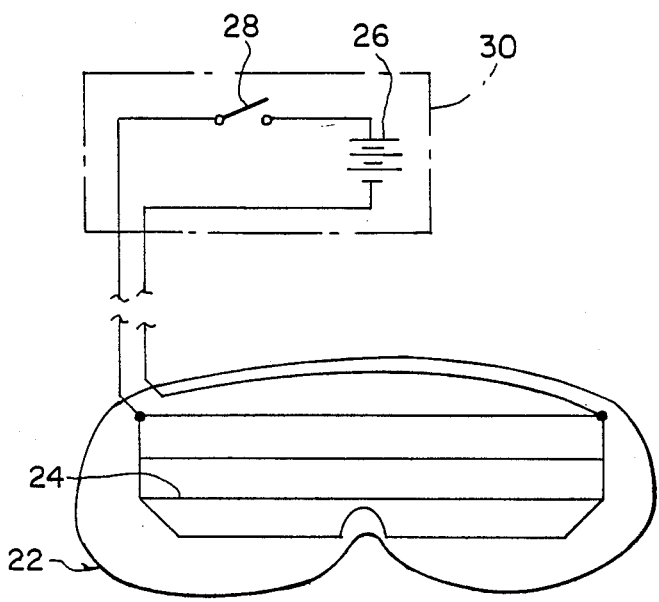
Figure 3
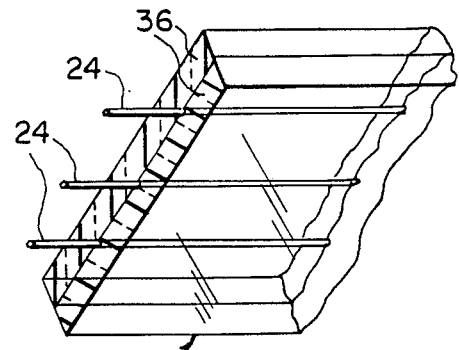
Figure 4

ELECTRICALLY HEATED SKI GOGGLES

BACKGROUND OF THE INVENTION

1. Field of the Invention

The instant invention relates generally to protective spectacles and more specifically it relates to an improved ski goggles that will remove frost and fog thereon.

2. Description of the Prior Art

Numerous protective spectacles have been provided in prior art that are adapted to prevent fogging and frosting of the lenses. For example, U.S. Pat. Nos. 2,539,284; 3,160,735 and 4,209,234 all are illustrative of such prior art. While these units may be suitable for the particular purpose to which they address, they would not be as suitable for the purposes of the present invention as heretofore described.

SUMMARY OF THE INVENTION

A primary object of the present invention is to provide an improved ski goggles that will overcome the shortcomings of the prior art devices.

Another object is to provide an improved ski goggles which includes a protective lens that has a fine grid of heat generating wire with sufficient resistance to produce enough heat to remove frost and fog from the lens.

An additional object is to provide an improved ski goggles that includes an external or self contained battery pack and switching device to supply electricity to the resistance wire grid.

A further object is to provide an improved ski goggles that is simple and easy to use.

A still further object is to provide an improved ski goggles that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 1 is a front view of a head of a skier wearing the invention with the battery pack and switch mounted on the frame of the goggles.

FIG. 2 is a side view of the skier wearing the invention with the battery pack and switch mounted on the belt of the skier.

FIG. 3 is a diagrammatic schematic view showing the electric circuit thereof.

FIG. 4 is a cross sectional perspective view of a portion of the lens showing the resistance wire laminated, embedded or otherwise affixed within the lens.

FIG. 5 is a cross sectional perspective view of a portion of the lens showing the resistance wires attached to either inner or outer surface of the lens.

DETAILED DESCRIPTION OF THE PREFERRED EMBODIMENTS

Turning now descriptively to the drawings, in which similar reference characters denote similar elements throughout the several views, FIGS. 1 through 5 illustrate an improved ski goggles 10 consisting of a frame 12 that has a plurality of vent holes 14 which are disposed on a front surface thereof as illustrated in FIG. 1 so that said holes are in line with the direction of travel of the skier (see FIG. 2). The frame 12 is worn on a face 16 in front of the eyes 18 of a skier 20 and a lens 22 is supported in the frame 12 to protect the eyes 18. A fine resistance wire grid 24 extends across the lens 22, whereby a power source 26 is connected to the resistance wire grid 24 for supplying electricity thereto and producing enough heat to remove frost and fog from the lens 22. A switch 28 is connected between the power source 26 and the resistance wire 24 to turn the supply of electricity on and off when so desired by the skier 20.

The resistance wire grid 24 is fabricated out of heat generating material and the power source 26 is a battery, wherein the battery and the switch 28 are disposed within a housing 30. FIG. 1 shows the housing 30 mounted on one side of the frame 12 while FIG. 2 shows the housing 30 mounted on a belt 32 of the skier with an elongated expansion cord 34 extending between the housing 30 and the heat generating resistance wire grid 24. FIG. 4 shows the heat generating resistance wire grid 24 laminated between two transparent layers 36 of the lens 22 while FIG. 5 shows the heat generating resistance wire grid 24 attached to outer surface 38 of the lens 22.

It will be understood that each of the elements described above, or two or more together, may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. An improved ski goggles which comprises:
   (a) a frame having a front surface containing a plurality of vent holes, said vent holes being disposed on said front surface of said frame and in line with the direction of travel of the skier so the the motion of the skier causes forced ventilation allowing air to more readily enter the goggles, said frame worn on a face in front of the eyes of the skier;
   (b) a lens supported in said frame to protect the eyes said lens being connected directly to said frame;
   (c) a fine resistance wire grid extending across said lens;
   (d) a power source electrically connected to said resistance wire grid for supplying electricity thereto so that enough heat to remove frost and fog from said lens is produced; and
   (e) a switch connected between said power source and said resistance wire to turn the supply of electricity on and off when so desired by the skier, said power source and said switch forming an integral unit disposed on said frame, so that said power source and said switch form a compact integral unit that is not bulky and does not interfere with the ears of the skier.

2. An improved ski goggles as recited in claim 1, wherein said power source is a battery.

3. An improved ski goggles as recited in claim 2, wherein said battery and said switch are disposed within a housing.

4. An improved ski goggles as recited in claim 3, wherein said housing is mounted on either side of said frame.

5. An improved ski goggles as recited in claim 3, wherein said housing is mounted on belt of the skier with an elongated expansion cord extending between said housing and said heat generating resistance wire grid.

6. An improved ski goggles as recited in claim 3, wherein said heat generating resistance wire grid is laminated between two transparent layers of said lens.

7. An improved ski goggles as recited in claim 3, wherein said heat generating resistance wire grid is embedded between two transparent layers of said lens.

8. An improved ski goggles as recited in claim 3, wherein said heat generating resistance wire grid is otherwise affixed between two transparent layers of said lens.

9. An improved ski goggles as recited in claim 3, wherein said heat generating resistance wire grid is attached to inner surface of said lens.

10. An improved ski goggles as recited in claim 3, wherein said heat generating resistance wire grid is attached to outer surface of said lens.

* * * * *